United States Patent
Ziberstein et al.

(10) Patent No.: US 9,107,578 B2
(45) Date of Patent: Aug. 18, 2015

(54) PANORAMIC ORGAN IMAGING

(71) Applicant: Gyrus ACMI, Inc., Southborough, MA (US)

(72) Inventors: Chaya Ziberstein, Zichron Yaakov (IL); Stuart Wolf, Yokneam (IL); Shai Finkman, Haifa (IL)

(73) Assignee: GYRUS ACMI, INC., Southborough, MA (US)

( * ) Notice: Subject to any disclaimer, the term of this patent is extended or adjusted under 35 U.S.C. 154(b) by 209 days.

(21) Appl. No.: 13/854,095

(22) Filed: Mar. 31, 2013

(65) Prior Publication Data

US 2014/0296644 A1    Oct. 2, 2014

(51) Int. Cl.
  *A61B 1/06* (2006.01)
  *A61B 1/00* (2006.01)
  *G06K 9/00* (2006.01)
  *G06K 9/36* (2006.01)

(52) U.S. Cl.
  CPC .......... *A61B 1/00183* (2013.01); *A61B 1/00009* (2013.01); *A61B 1/00172* (2013.01); *A61B 1/06* (2013.01); *A61B 1/0638* (2013.01)

(58) Field of Classification Search
  CPC ............. A61B 1/00009; A61B 1/0005; A61B 1/00096; A61B 1/00193; A61B 5/0062; H04N 2005/2255; H04N 5/23238; H04N 1/3876; G06T 3/4038; G06T 7/0024
  See application file for complete search history.

(56) References Cited

U.S. PATENT DOCUMENTS

| | | | |
|---|---|---|---|
| 5,140,647 A | 8/1992 | Ise et al. | |
| 5,372,502 A | 12/1994 | Massen et al. | |
| 5,827,176 A | 10/1998 | Tanaka et al. | |
| 6,978,052 B2 | 12/2005 | Beged-Dov et al. | |
| 7,381,183 B2 | 6/2008 | Hale et al. | |
| 7,744,528 B2 | 6/2010 | Wallace et al. | |
| 7,794,338 B2 | 9/2010 | Cherry | |
| 7,813,538 B2 | 10/2010 | Carroll et al. | |

(Continued)

FOREIGN PATENT DOCUMENTS

| | | | |
|---|---|---|---|
| JP | H01113717 A | 5/1989 | |
| JP | 1164352 A | 6/1989 | |

(Continued)

OTHER PUBLICATIONS

International Application # PCT/US14/31588 Search Report dated Jul. 25, 2014.

*Primary Examiner* — Anhtuan T Nguyen
*Assistant Examiner* — Alexandra Newton
(74) *Attorney, Agent, or Firm* — D. Kligler I.P. Services Ltd.

(57) ABSTRACT

An imaging apparatus, including a pattern projecting device that projects a pattern onto a wall of a body cavity, the pattern including at least a first section and a second section. The apparatus also includes an illumination device that directs an illumination light onto the wall of the body cavity and an imaging device that, while in a first orientation directed to the first section of the pattern projected onto the wall, acquires a first image of the first section, and while in a second orientation directed to the second section of the pattern projected onto the wall, acquires a second image of the second section. The apparatus further includes a processor controlling the pattern projecting device and the illumination device such that the imaging device acquires the first and the second images during the use of the illumination light, and stitching the first image to the second image.

9 Claims, 11 Drawing Sheets

(56) References Cited

U.S. PATENT DOCUMENTS

| | | |
|---|---|---|
| 7,922,652 B2 | 4/2011 | Yagi et al. |
| 2003/0142882 A1* | 7/2003 | Beged-Dov et al. .......... 382/284 |
| 2006/0195014 A1 | 8/2006 | Seibel et al. |
| 2007/0001618 A1 | 1/2007 | Jeon et al. |
| 2007/0161854 A1 | 7/2007 | Alamaro et al. |
| 2008/0058593 A1 | 3/2008 | Gu et al. |
| 2009/0177034 A1 | 7/2009 | Urakawa et al. |
| 2009/0208143 A1 | 8/2009 | Yoon et al. |
| 2010/0076261 A1 | 3/2010 | Neeman et al. |
| 2010/0149183 A1 | 6/2010 | Loewke et al. |
| 2010/0165087 A1 | 7/2010 | Corso et al. |
| 2013/0030250 A1* | 1/2013 | Findeisen et al. ............. 600/165 |
| 2014/0071239 A1 | 3/2014 | Yokota |
| 2014/0248576 A1* | 9/2014 | Tchouprakov et al. ......... 433/30 |

FOREIGN PATENT DOCUMENTS

| | | |
|---|---|---|
| JP | H5052533 A | 3/1993 |
| WO | 9827514 A2 | 6/1998 |
| WO | 2004111937 A1 | 12/2004 |
| WO | 2009102445 A2 | 8/2009 |
| WO | 2012161244 A1 | 11/2012 |

* cited by examiner

PANORAMIC ORGAN IMAGING

FIELD OF THE INVENTION

The present invention relates generally to imaging of a body cavity, and specifically to an endoscope that is able to acquire a panoramic image of the body cavity.

BACKGROUND OF THE INVENTION

While an endoscope may provide an image of a section of walls of a body cavity, the image provided may be insufficient for a professional viewing the image. Typically, if only a section of the walls is imaged, the professional may not be able to correctly relate the imaged section with other parts of the body cavity walls. Availability of a panoramic image of the body cavity walls overcomes a lack of correlation and orientation which occurs if only a portion of the walls are imaged.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides an imaging apparatus, including:

a pattern projecting device configured when in use to project a pattern onto a wall of a body cavity, wherein the pattern includes at least a first section and a second section;

an illumination device configured to direct an illumination light onto the wall of the body cavity;

an imaging device configured when in use and while in a first orientation directed to the first section of the pattern projected onto the wall, to acquire a first image of the first section, and when in use and while in a second orientation directed to the second section of the pattern projected onto the wall, to acquire a second image of the second section; and a processor, configured to control the pattern projecting device and the illumination device such that the imaging device acquires the first and the second images during the use of the illumination light, and stitches the first image to the second image.

Typically, the processor is configured to switch between the pattern projecting device and the illumination device intermittently so as to toggle the pattern projecting device and the illumination device. The pattern and the illumination light may be visible light. The imaging device may be configured in the first orientation to acquire a third image of the pattern, and in the second orientation to acquire a fourth image of the pattern, and the processor may be configured to stitch the first image to the second image using the third and fourth images as fiducials.

In a disclosed embodiment the processor is configured to activate the illumination device and the pattern projecting device simultaneously. Typically, the pattern projecting device is configured to project the pattern at a first wavelength, and the illumination device is configured to generate the illumination light at a second wavelength different from the first wavelength. The processor may generate a stitched image by stitching the first and the second image, and may be further configured to filter pattern-images, generated in response to the first wavelength, from the stitched image so as to generate a filtered stitched image.

In a further disclosed embodiment the imaging device is configured to acquire a pattern-image of the pattern, and the pattern is configured so that the acquired pattern-image defines a unique direction of view of the imaging device. Typically, the pattern is configured so that the acquired pattern-image defines a unique orientation of the imaging device.

In a yet further disclosed embodiment the pattern projecting device includes a light guide and a diffractive optic element.

In an alternative embodiment the illumination device includes a light guide and a light source.

In a further alternative embodiment the imaging device includes an endoscope.

In a yet further alternative embodiment the imaging device includes a first sensor responsive to a first wavelength and a second sensor responsive to a second wavelength different from the first wavelength, and the pattern projecting device is configured to project the pattern at the first wavelength and the illumination device is configured to generate the illumination light at the second wavelength.

Typically, the pattern projecting device is fixed in a given position so that the pattern projected onto the wall is immobile.

There is further provided, according to an embodiment of the present invention, a method, including:

projecting a pattern onto a wall of a body cavity, wherein the pattern includes at least a first section and a second section;

directing an illumination light onto the wall of the body cavity;

acquiring, using an imaging device configured when in use and while in a first orientation directed to the first section of the pattern projected onto the wall, a first image of the first section;

acquiring, using the imaging device when in use and while in a second orientation directed to the second section of the pattern projected onto the wall, a second image of the second section; and controlling the pattern projecting device and the illumination device such that the imaging device acquires the first and the second images during the use of the illumination light, and stitches the first image to the second image.

The present invention will be more fully understood from the following detailed description of the embodiments thereof, taken together with the drawings in which:

DETAILED DESCRIPTION OF EMBODIMENTS

Overview

An embodiment of the present invention provides imaging apparatus and a method for generating a panoramic image of a body cavity, such as a bladder. The imaging apparatus comprises a pattern projecting device, an illumination device, and an imaging device, typically an endoscope, and the apparatus is configured to be inserted into the body cavity. Once inserted into the body cavity, the pattern projecting device may be fixed in place and then may be activated to project an immobile pattern onto walls of the body cavity. In addition, the illumination device may be activated to illuminate the walls of the body cavity, typically with white light.

In some embodiments the illumination device and the pattern projecting device are activated simultaneously. In other embodiments the illumination device and the pattern projecting device are toggled. Wavelengths of the light from the two devices may be different, for example the pattern may be projected with infra-red light, whereas the illumination light may comprise visible light. Alternatively, wavelengths of the light from the two devices may be substantially the same, for example both the pattern and the illumination may use visible light.

The imaging device is moved from a first orientation to a second orientation. In the first orientation the imaging device acquires a first image, which in some embodiments comprises an image of a first section of the pattern projected onto the walls of the body cavity as well as an image of the first section of the walls themselves, the latter being formed from the illumination light. Similarly in the second orientation the imaging device acquires a second image, which may comprise an image of a second section of the pattern projected onto the walls as well as an image of the second section of the walls.

Since the pattern is immobile, a processor may use the pattern images (comprised in the first and second images) as fiducials in order to stitch the first and the second images together.

The imaging device may be moved in an iterative manner to further orientations, and may acquire respective further images of the pattern projected onto the walls as well as of the walls themselves in the further orientations. The further images may be stitched, as described above, so that with sufficient iterations the process is able to generate a panoramic image of the body cavity.

DETAILED DESCRIPTION

Figure 1:
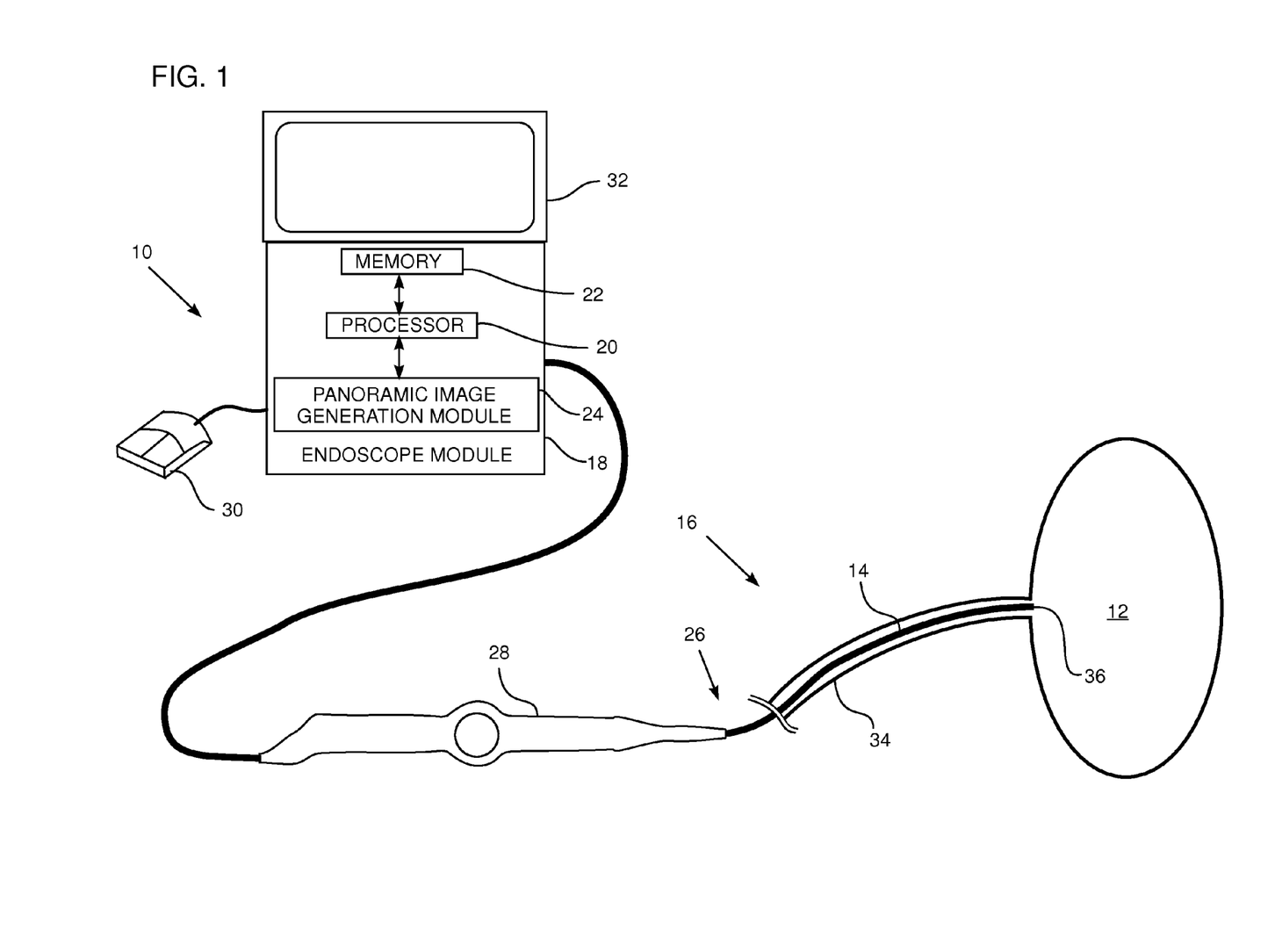
FIG. 1 is a schematic illustration of a panoramic imaging system, according to an embodiment of the present invention.

Reference is now made to FIG. 1, which is a schematic illustration of a panoramic endoscopic imaging system 10, according to an embodiment of the present invention. System 10 may be used in an invasive medical procedure, typically a minimally invasive procedure, on a body cavity 12 of a human patient in order to image substantially the whole of the body cavity in a panoramic manner. By way of example, in the present description the body cavity is assumed to be the bladder of a patient, and body cavity 12 is also referred to herein as bladder 12. However, it will be understood that system 10 may be used to image substantially any human body cavity, such as the gastrointestinal organs, the bronchium, the chest, or on a non-human cavity.

System 10 comprises an imaging apparatus 14 which enables delivery of an endoscope 16 to bladder 12. Apparatus 14 is typically in the form of a tube which is able to traverse a lumen of a patient's body. Endoscope 16, operational and structural details of which are described below, is controlled by an endoscope module 18 having a processor 20 communicating with a memory 22. Endoscope module 18 also comprises a panoramic image generation module 24, whose functions are described below, and which may be implemented in software, hardware, or a combination of software and hardware. Apparatus 14 is connected at its proximal end 26 to a handle 28 which enables an operator, herein assumed to be a physician, of system 10 to insert the apparatus into the bladder as well as to manipulate the endoscope so as to acquire images of the bladder. In some embodiments of the present invention, rather than manual manipulation of endoscope 16 using handle 28, the endoscope is manipulated automatically, such as by scanning, so as to acquire its images. U.S. Patent Application 2009/0177034, which is incorporated herein by reference, describes a method for automatic scanning of an endoscope, and the method may be adapted, mutatis mutandis, for embodiments of the present invention wherein automatic scanning is used. For simplicity, except where otherwise stated, in the following description manual endoscope manipulation using handle 28 is assumed, and those having ordinary skill in the art will be able to adapt the description for the case of automatic endoscope manipulation.

The operator is able to provide input to module 18 via controls 30, which typically comprise at least one of a keyboard, a pointing device, or a touch screen. Alternatively or additionally, at least some of controls 30 may be incorporated in handle 28. For simplicity, controls 30 are herein assumed to comprise a mouse, so that the controls are also referred to herein as mouse 30. Apart from image generation module 24, endoscope module 18 typically also comprises other modules, such as a graphic user interface (GUI) module, which may be used by the operator of system 10 in operating the endoscope module; for simplicity these modules are not shown in the figure.

The processor uses software, typically stored in memory 22, to control system 10. Results of the actions performed by processor 20 may be presented on a screen 32 to the operator of system 10, the screen typically displaying a panoramic image of bladder 12 that is generated by system 10. The software for operating system 10 may be downloaded to processor 20 in electronic form, over a network, for example, or it may, alternatively or additionally, be provided and/or stored on non-transitory tangible media, such as magnetic, optical, or electronic memory.

To operate system 10, the physician inserts apparatus 14 through a urethra 34 until a distal end 36 of the apparatus enters the bladder.

Figure 2A:
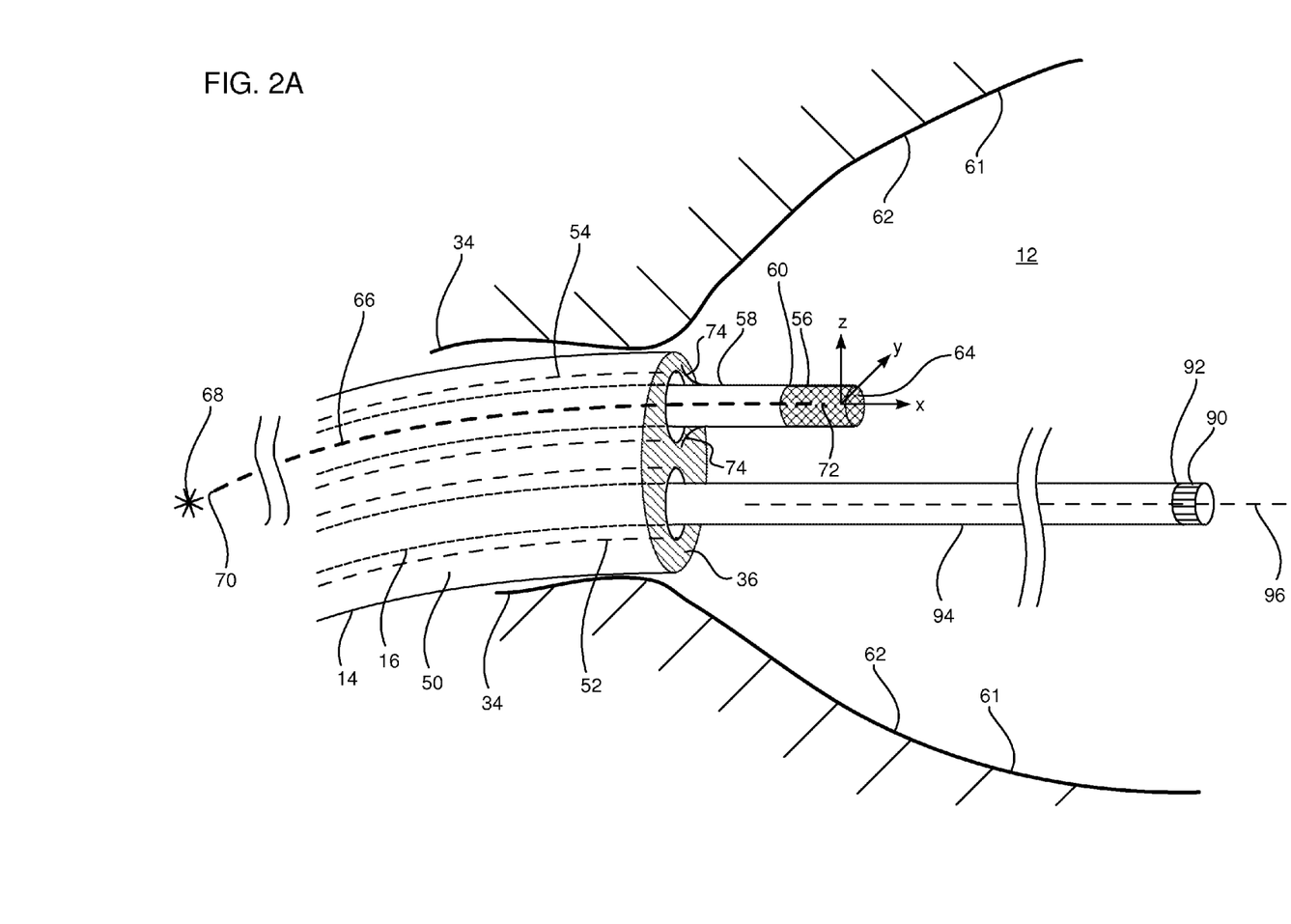
FIG. 2A is a schematic illustration of a distal end of the panoramic imaging system, according to an embodiment of the present invention.

FIG. 2A is a schematic diagram illustrating distal end 36 of apparatus 14 as the apparatus enters bladder 12, according to an embodiment of the present invention. Apparatus 14 is formed as a tubular member 50, the tubular member typically having a circular cross-section. Within member 50 are formed two channels: an endoscope channel 52 is used to convey endoscope 16 to bladder 12; and a projector channel 54 is used to convey a pattern projecting device 56, herein also termed a projector 56, to bladder 12. Channels 52 and 54 are typically substantially parallel to each other. A projector holding tube 58 is used to fixedly retain the projector at a distal end 60 of the holding tube.

Projector 56 is constructed so as to project a pattern 61 onto walls 62 of the bladder. The projector is configured so that pattern 61 is projected onto substantially all of walls 62, and the projected pattern is assumed to be characterized in terms of an arbitrary set of orthogonal xyz axes having their origin at projector 56, the axes also being referred to herein as the projector axes. The type and characteristics of the pattern projected are explained in more detail below with respect to FIG. 5. In order to generate the pattern, projector comprises at least one diffractive optical element (DOE) 64, which is fabricated so that, when illuminated by coherent light, a desired pattern projects from the projector. For simplicity, the following description assumes, except where otherwise stated, that pattern 61 is generated using one DOE 64, which is typically approximately cylindrical, and which is illuminated by one single coherent light source. Those having ordinary skill in the art will be able to adapt the description for the case of multiple DOEs 64 illuminated by a single coherent light source, or for the case of multiple DOEs 64 illuminated by multiple coherent light sources.

In one embodiment the coherent light for DOE 64 is delivered to the DOE by a single mode fiber optic light guide 66 which is enclosed within holding tube 58. A laser 68, typically a laser diode, is coupled to a proximal end 70 of the fiber optic, so as to inject the coherent light into the optic. The coherent light exits from a distal end 72 of the fiber optic so as to illuminate DOE 64. Typically, laser 68 may be incorporated into handle 28, and may be powered by endoscope module 18.

Alternatively, laser 68 may be located at distal end 60 of tube 58, and may be configured to illuminate DOE 64 directly. In this case, while there is no need for fiber optic 66, power for laser 68 may be transferred from module 18 by conductors (not shown in the diagram) within tube 58.

During operation of system 10, projector 56 is fixedly attached to tubular member 50. In one embodiment the attachment is achieved using springs 74 which are connected to holding tube 58. The springs hold tube 58 in place by pushing against distal end 36 of the tubular member. However, the attachment may be by any other convenient method known in the art.

Endoscope 16 comprises an optical imaging section 90, an embodiment of which is described in more detail with reference to FIG. 3A below. Imaging section 90 is located at a distal end 92 of an endoscope tube 94, which has a central axis of symmetry 96. In contrast to projector 56, section 90 is able to move with respect to member 50. For a flexible or for a rigid endoscope the movement may comprise rotation about axis 96, as well as translation along the axis. In some embodiments, depending on the construction of endoscope 16, the movement of section 90 may also comprise translation of the section orthogonally to axis 96. Such an orthogonal translation of the imaging section may be accomplished, for a flexible endoscope having a bending section and/or a rotatable imaging unit, by bending of distal end 92 of the endoscope with respect to axis 96. Typically, all movements of section are by an operator of system 10 manipulating controls in handle 28.

Figure 2B:
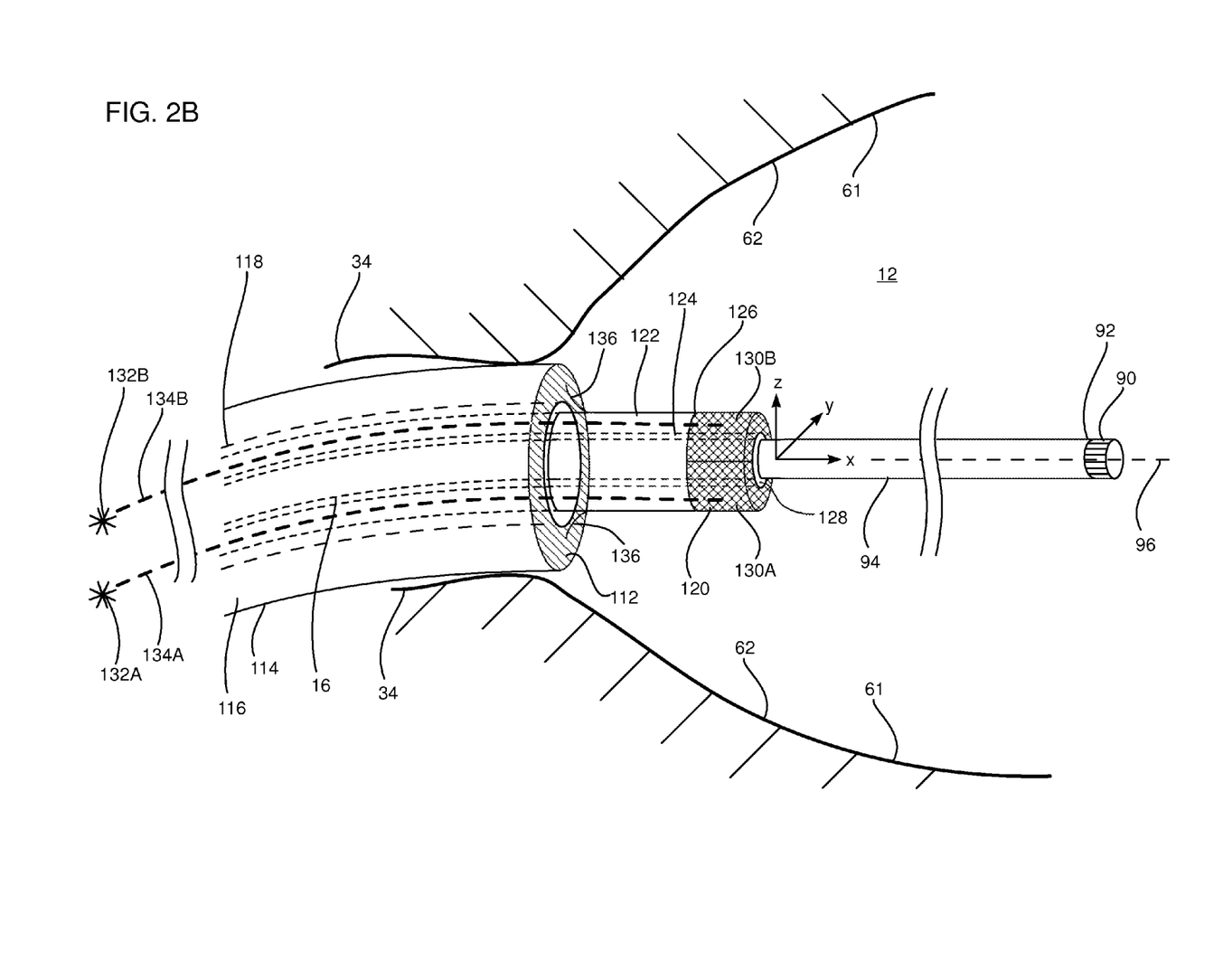
FIG. 2B is a schematic illustration of a distal end of the panoramic imaging system, according to an alternative embodiment of the present invention.

FIG. 2B is a schematic diagram illustrating a distal end 112 of an imaging apparatus 114 as the apparatus enters bladder 12, according to an alternative embodiment of the present invention. Apart from the differences described below, the operation of imaging apparatus 114 is generally similar to that of imaging apparatus 14 (FIGS. 1 and 2A), and elements indicated by the same reference numerals in apparatus 14 and apparatus 114 are generally similar in construction and in operation. In contrast to apparatus 14, apparatus 114 is formed as a tubular member 116 within which is formed a single channel 118. Single channel 118 is used to convey both endoscope 16 and a pattern projecting device 120, herein also termed projector 120, to the bladder, the endoscope and projector being arranged to be coaxial with each other, in contrast to the parallel arrangement of apparatus 14.

A projector holding tube 122 is formed as a generally cylindrical tube which is able to traverse channel 118. Tube 122 has a central cylindrical conduit 124 that is configured to convey endoscope tube 94 within the conduit, and projector 120 is fixed to a distal end 126 of the projector holding tube.

Projector 120 is formed as a cylinder with a central aperture 128 so that the projector aligns and mates with distal end 126. As for projector 56, projector 120 is constructed so as to project pattern 61 onto walls 62 of the bladder, and the projector comprises at least one DOE 130 which generates the pattern when illuminated by coherent light.

By way of example projector 120 is assumed to comprise a DOE 130A and a DOE 130B. DOE 130A and DOE 130B are typically approximately semi-cylindrical, and are respectively illuminated with coherent light by lasers 132A and 132B which transmit the light via respective single mode fiber optics 134A and 134B. However, the coherent light supplying the at least one DOE of projector 120 may be by any of the methods described above for apparatus 14.

As for apparatus 14, during operation of system 10 projector 120 is fixedly attached to tubular member 116. The attachment may be by springs 136 which are connected to the external wall of projector holding tube 122, and which hold the tube and projector in place by pushing against distal end 112 of the tubular member. Once the projector is fixed in place, imaging section 90 of endoscope 16 may be manipulated generally as described above for apparatus 14. Thus, for a flexible or a rigid endoscope section 90 may be rotated about axis 96 or translated along the axis by rotating or sliding tube 94 within conduit 124. If endoscope 16 is flexible its section 90 may be translated orthogonally to axis 96, as described above for apparatus 14.

Figure 3A:
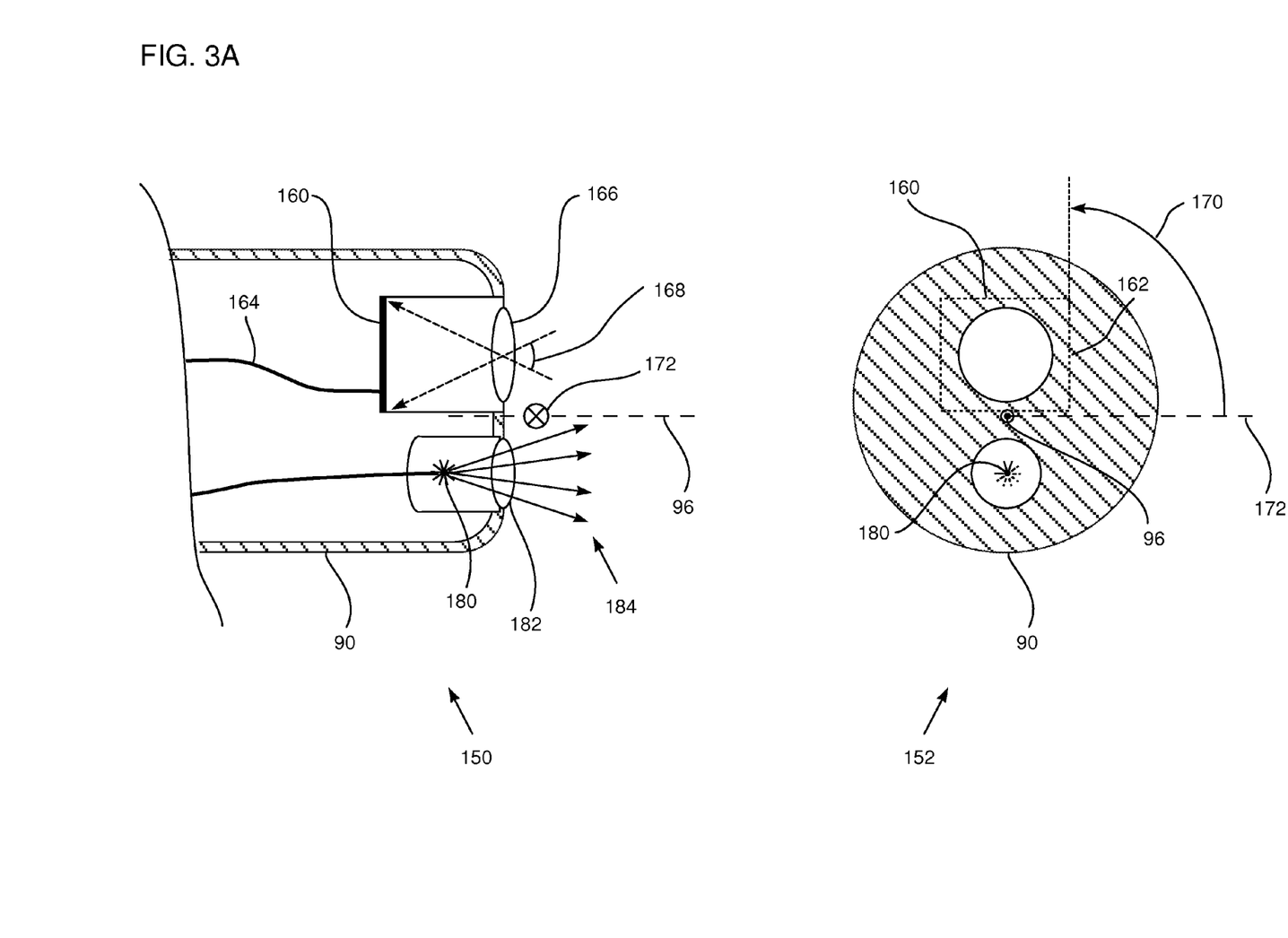
FIG. 3A is a schematic illustration of an optical imaging section, according to an embodiment of the present invention.

FIG. 3A is a schematic illustration of optical imaging section 90, according to an embodiment of the present invention. The figure illustrates a schematic cross-sectional side view 150 of section 90, and a schematic cross-sectional front view 152 of the section. Section 90 comprises an imaging device 160, typically a rectangular array of charge coupled devices (CCDs) which acts as an image sensor. A direction of a side 162 of the device may be used to define an orientation of the device. Device 160 receives power and controls for its operation from endoscope module 18, via a cable 164, and the cable is also configured to convey signals from device 160, representative of images acquired by the device, to the module. Device 160 is configured to use imaging optics 166 to acquire images of sections of walls 62 that are within a field of view 168 of the device. A given image of walls 62 (including projections from projector 56 or projector 120 onto the walls) that is acquired by device 160 is defined by field of view 168, which is in turn defined by optics 166, a direction of axis 96, and an angular orientation 170 of the device about axis 96, measured with respect to an arbitrary axis 172 in a plane orthogonal to axis 96. (The image is also defined by the position and orientation of device 160 with respect to walls 62.) By way of illustration, for side view 150 axis 172 is assumed to be into the plane of the paper, and angular orientation 170 is assumed to be measured between axis 172 and side 162.

Imaging section 90 also comprises an illumination device 180, typically comprising a light emitting diode (LED), which optionally may use associated optical elements 182 to direct illumination light 184 onto walls 62. Device 180 and elements 182, if used, are configured to direct light 184 to the region being imaged by imaging device 160. The illumination light, after reflection and/or scattering from the walls, is used by imaging device 160 in order to acquire its images.

Figure 3B:
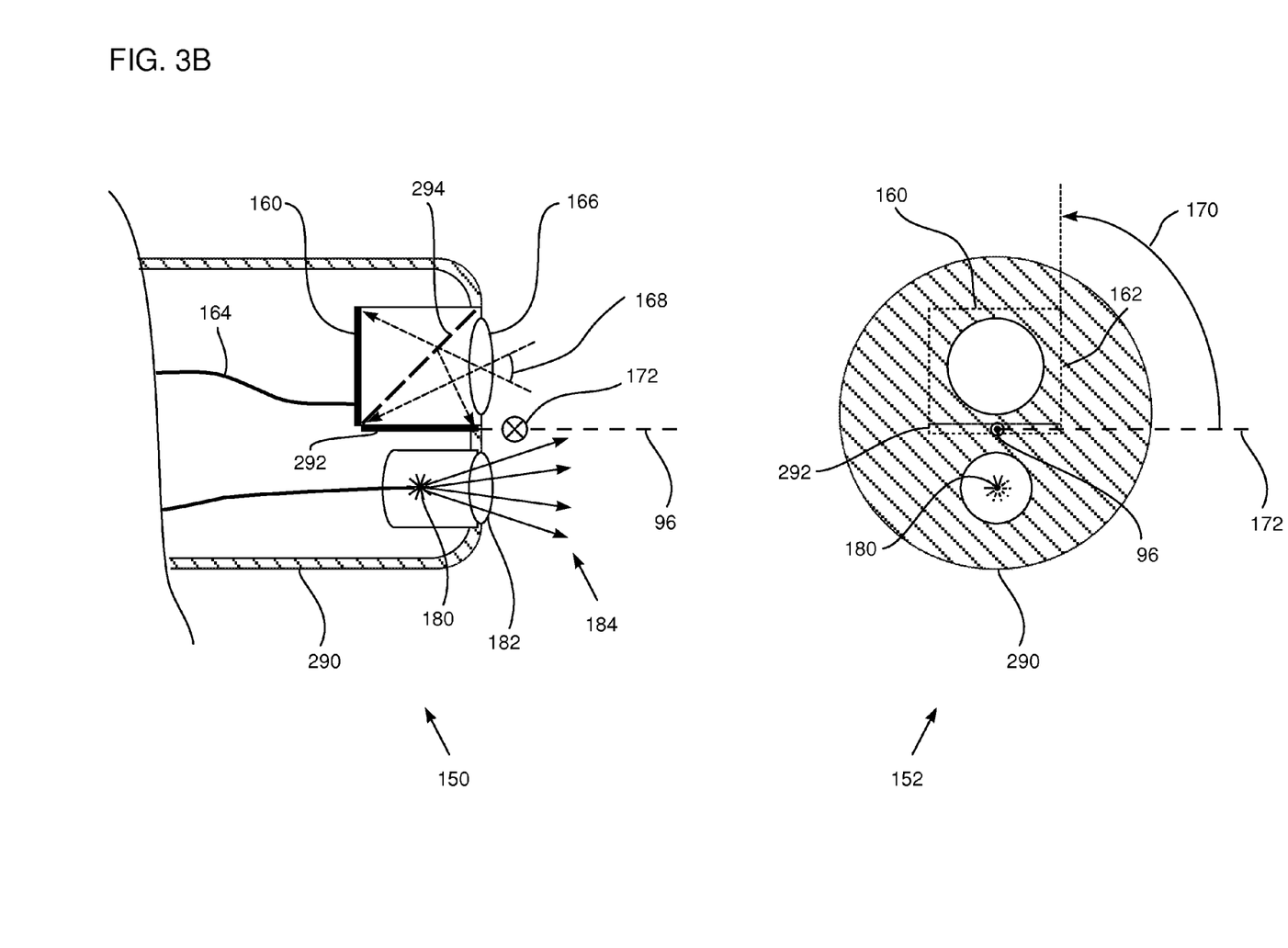
FIG. 3B is a schematic illustration of an optical imaging section 290, according to an alternative embodiment of the present invention.

FIG. 3B is a schematic illustration of an optical imaging section 290, according to an alternative embodiment of the present invention. Apart from the differences described below, the operation of section 290, which is located at distal end of tube 94, is generally similar to that of section 90 (FIG. 3A), and elements indicated by the same reference numerals in both sections 90 and 290 are generally similar in construction and in operation.

In addition to imaging device 160, section 290 comprises a second imaging device 292 which is substantially similar in operation to device 160, and which acts as a second image sensor. Device 292 is configured to receive illumination from the same elements that are imaged by device 160, and to receive its power, and convey its acquired images via cable 164. Typically, as described in more detail below, the spectrum of light imaged by device 292 is different from that of device 160, and the different spectra may be provided to the two devices using a partially reflecting element 294, which is configured to selectively reflect and transmit light in predetermined spectral ranges to the two devices. In one embodiment devices 160 and 292 are mounted at right angles to each other, and element 294 comprises a dichroic mirror which is oriented at 45° to the two devices. The dichroic mirror transmits light in a first spectral range to device 160, and reflects light in a second spectral range to device 292. In an alternative embodiment element 294 comprises a broadband beamsplitter, and the sensitivity of devices 160 and to their different spectral ranges is achieved by incorporating respective filters (not shown in the figure) before the devices. However, imaging of the different spectral ranges on the two imaging device sensors may be any other convenient system known in the art.

Figure 4:
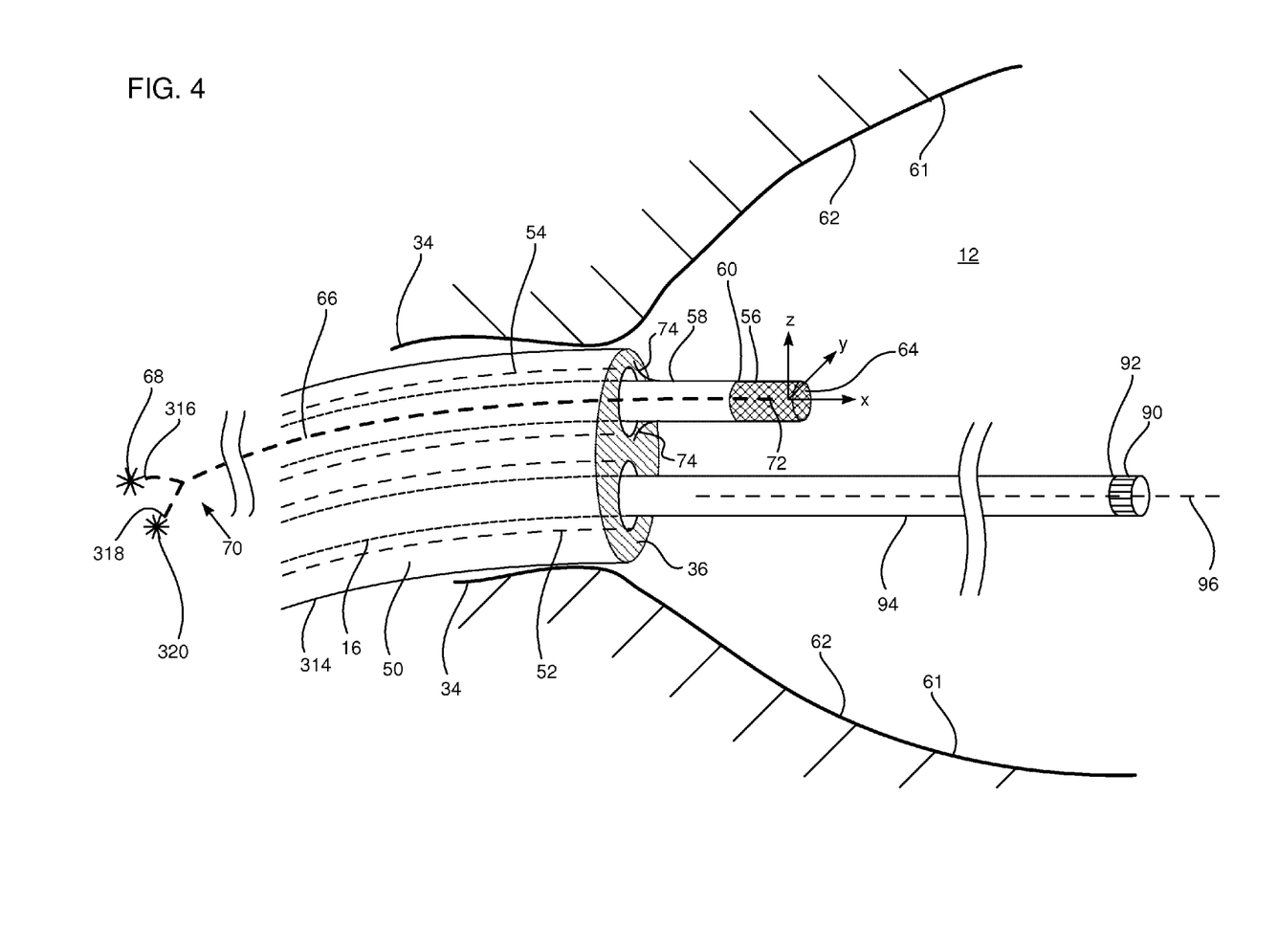
FIG. 4 is a schematic diagram illustrating a distal end of the panoramic imaging system, according to a further alternative embodiment of the present invention.

FIG. 4 is a schematic diagram illustrating distal end 36 of an apparatus 314 as the apparatus enters bladder 12, according to an alternative embodiment of the present invention. Apart from the differences described below, the operation of apparatus 314 is generally similar to that of apparatus 14 (FIG. 2A), and elements indicated by the same reference numerals in both apparatus 14 and apparatus 314 are generally similar in construction and in operation.

In contrast to apparatus 14, in apparatus 314 proximal end 70 of fiber optic 66 is bifurcated to terminate in a first proximal end 316 and a second proximal end 318. Laser 68 is coupled to first proximal end 316, and an illumination device 320, typically generally similar to illumination device 180 described above with reference to FIG. 3A, is coupled to second end 320. Laser 68 and device 320 may both inject the light they generate into fiber optic 66 so that the generated light radiates from fiber optic distal end 72. Typically, the light generated by device 320 and radiating from fiber optic distal end 72 is configured to illuminate all of walls 62. It will be understood that in apparatus 314 light from device 320 radiates from projector 56, rather than, as in apparatus 14, light from device 180 radiating from distal end 92 of endoscope 16.

Figure 5:
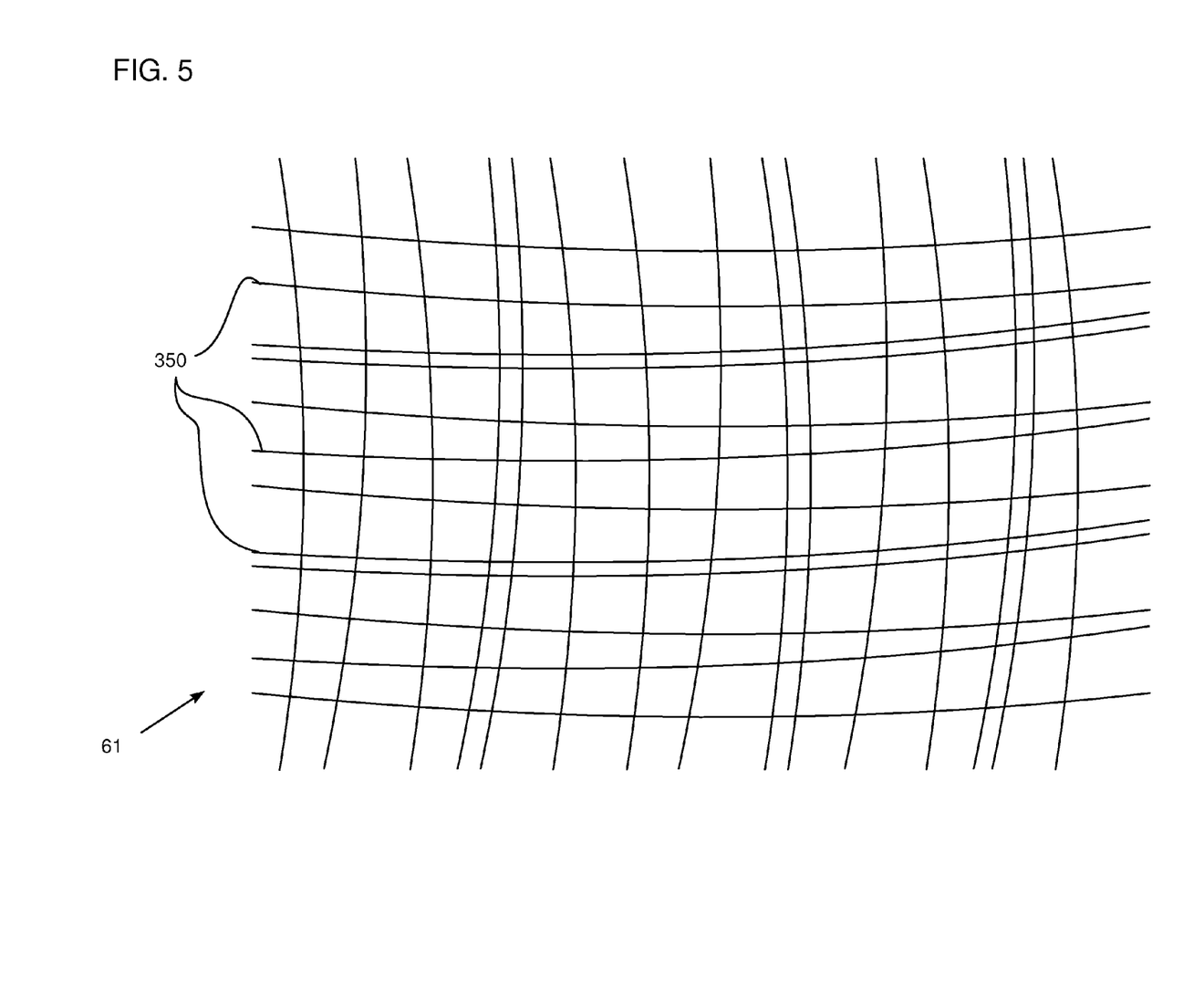
FIG. 5 is a schematic illustration of a portion of a pattern as imaged by an imaging device, according to an embodiment of the present invention.

FIG. 5 is a schematic illustration of a portion of pattern 61 as imaged by imaging device 160 or imaging device 292, according to an embodiment of the present invention. As explained above, pattern 61 is projected by projector 56 onto walls 62, the walls, in the case of bladder 12 or any other body cavity, comprising three-dimensional curved surfaces. In embodiments of the present invention, pattern 61 is configured so that the image formed on the imaging device by a portion of the pattern can be used by processor 20 (FIG. 1) to distinguish different directions of view of the imaging device towards walls 62, as well as to distinguish different orientations of the imaging device with respect to a given direction of view.

In other words, referring back to FIGS. 3A and 3B, pattern 61 is configured so that processor 20 is able to analyze the image of the pattern on device 160 or device 292 so as to determine a direction of view of the devices, measured with respect to the projector axes, that is unique. The direction of view corresponds to axis 96. Pattern 61 is also configured so that the image of pattern 61 on devices 160 or 292 enables processor 20 to determine a value of angular orientation 170 that is unique.

Herein, by way of example, pattern 61 is assumed to be formed of a plurality of lines 350 which are projected onto walls 62. Typically, as illustrated in the figure, the images of the lines as formed on device 160 are curved. The plurality of lines are formulated to have sufficient asymmetry and/or randomness in their geometrical distribution so that the image of the lines on the imaging device satisfies the requirements of uniqueness stated above, i.e., that processor 20 is able, by analysis of the imaged pattern, to distinguish unambiguously different directions of view and orientations of the imaging device.

Other forms of pattern 61 that satisfy the distinguishing requirements of non-ambiguity and uniqueness stated above will be apparent to those having ordinary skill in the art. Such forms include, but are not limited to, patterns comprising closed shapes, which may or may not be connected to each other, as well as patterns having lines similar to those depicted in FIG. 5, wherein the lines have different characteristics, such as differing thicknesses or curvatures.

Figure 6:
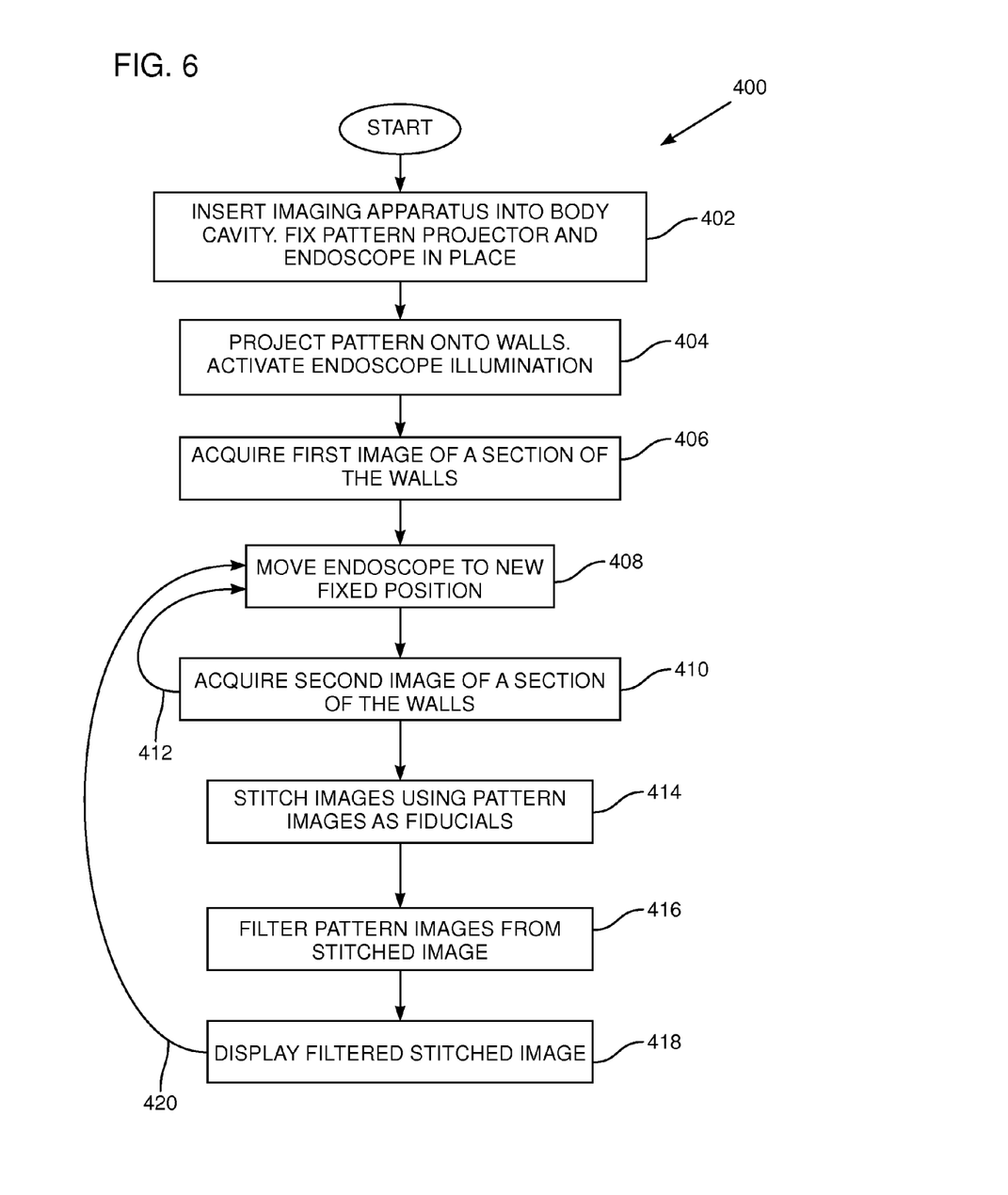
FIG. 6 is a flowchart of steps performed in generating a panoramic image of a bladder, according to an embodiment of the present invention.

In some embodiments of the present invention, the pattern projected onto the wall is implemented so that it divides the wall into sections that may be individually scanned. In this case the sections may be scanned in turn; the scanned sections may then be stitched together, generally as described below with respect to flowchart 400, mutatis mutandis.

FIG. 6 is a flowchart 400 of steps performed in generating a panoramic image of bladder 12, according to an embodiment of the present invention. The following description assumes that imaging apparatus 14 (FIG. 1 and FIG. 2A) is used to acquire images of the bladder, and that imaging section 90 of the apparatus is as described above with reference to FIG. 3A. The description also assumes that imaging device 160 is sensitive to the light projected by illumination device 180 and to the light from laser 68. Those having ordinary skill on the art will be able to adapt the description of flowchart 400, mutatis mutandis, if either imaging apparatus 114 or imaging apparatus 314 is used.

The wavelength of laser 68 is selected so that it is not within the spectrum of wavelengths of the light projected from illumination device 180. I.e., the two light sources project different wavelengths. For example, laser 68 may be chosen to project invisible infra-red light, whereas device 180 may be chosen to project light within the visible spectrum. While laser 68 may project a narrow band of wavelengths, device 180 typically projects a broad band of wavelengths corresponding to white light.

In a first step 402, apparatus 14 is inserted into bladder 12 until distal end 36 is within the bladder, generally as illustrated in FIG. 2A. Once distal end 36 is within the bladder, projector 56 is moved to protrude from the distal end, and the projector is fixed in place, typically by ensuring that springs 74 mate with the distal end. In addition, imaging section 90 is moved to a fixed arbitrary initial position within the bladder, so that it has a first orientation.

In an activation step 404, laser 68 is activated so as to project pattern 61 onto walls 62. Since projector 56 is fixed in place, projected pattern 61 is immobile and invariant with regard to walls 62. In addition, illumination device 180 of the endoscope is activated so that light 184 projects onto a region of walls 62.

In a first imaging step 406, device 160 acquires a first image of walls 62 within its field of view 168. The image acquired comprises elements of walls 62 as well as elements of pattern 61 that are within the field of view. Processor 20 stores the acquired image in memory 22.

In a motion step 408, imaging section 90 is moved from its initial position to a different, new, position, and the section is again fixed in place so that it has a second orientation. In motion step 408 pattern 61 remains fixed in place. The operator of system 10 may use handle 28 to implement the movement manually. Alternatively, if automatic scanning is implemented in system 10, the movement may be implemented automatically. The movement may comprise one or more of the possible motions of endoscope 16 described above with reference to FIG. 2A. Typically, the movement is implemented systematically, so that the endoscope is translated and/or rotated by a predetermined amount.

In some embodiments, the system 10 operator selects the amount of movement between the two positions by observing the image generated by imaging device 160 on screen 32. To facilitate selection of the new position, processor 20 may present the image stored in step 406, as well as an image generated by device 160 as endoscope 16 is moved. Typically, although not necessarily, the amount of movement to the new position is selected so that a portion of the image generated in the new position overlaps the image acquired in step 406.

In a second imaging step 410, once section 90 is fixed in its new position, device 160 acquires a second image of walls 62 and elements of pattern 61 within its field of view 168. Processor 20 stores the acquired second image in memory 22.

As illustrated by an arrow 412, steps 408 and steps 410 are repeated, so that the process of moving endoscope 16 to a new fixed position and orientation, and capturing an image at the new position and orientation, iterates. The iterations typically acquire multiple second images, and may be repeated until the image displayed in a step 418 (described further below) is accepted by the system 10 operator.

In a stitching step 414 processor 20 stitches the first and second images, using the images of pattern 61 as fiducials for performing the stitching. In other words, the processor aligns the sections of the patterns in the first and second images with each other. The stitching generates a panoramic image, herein referred to as an unfiltered panoramic image, which comprises images of walls 62 together with images of pattern 61.

In a filtration step 416, processor 20 digitally filters the unfiltered panoramic image, so as to remove the images of pattern 61 and generate a filtered stitched panoramic image which does not include pattern 61. The digital filtration may use the fact that the spectra of laser 68 and device 180 are different. Alternatively or additionally, the digital filtration may use characteristics of the image of pattern 61, for example that the image comprises substantially continuous lines, to perform the filtration.

In presentation step 418, processor 20 presents the filtered stitched panoramic image on screen 32. If required, for example to expand the area of walls 62 that have been acquired and displayed in step 418, the system 10 operator may return the flowchart to motion step 408, as illustrated by an arrow 420.

Figure 7A:
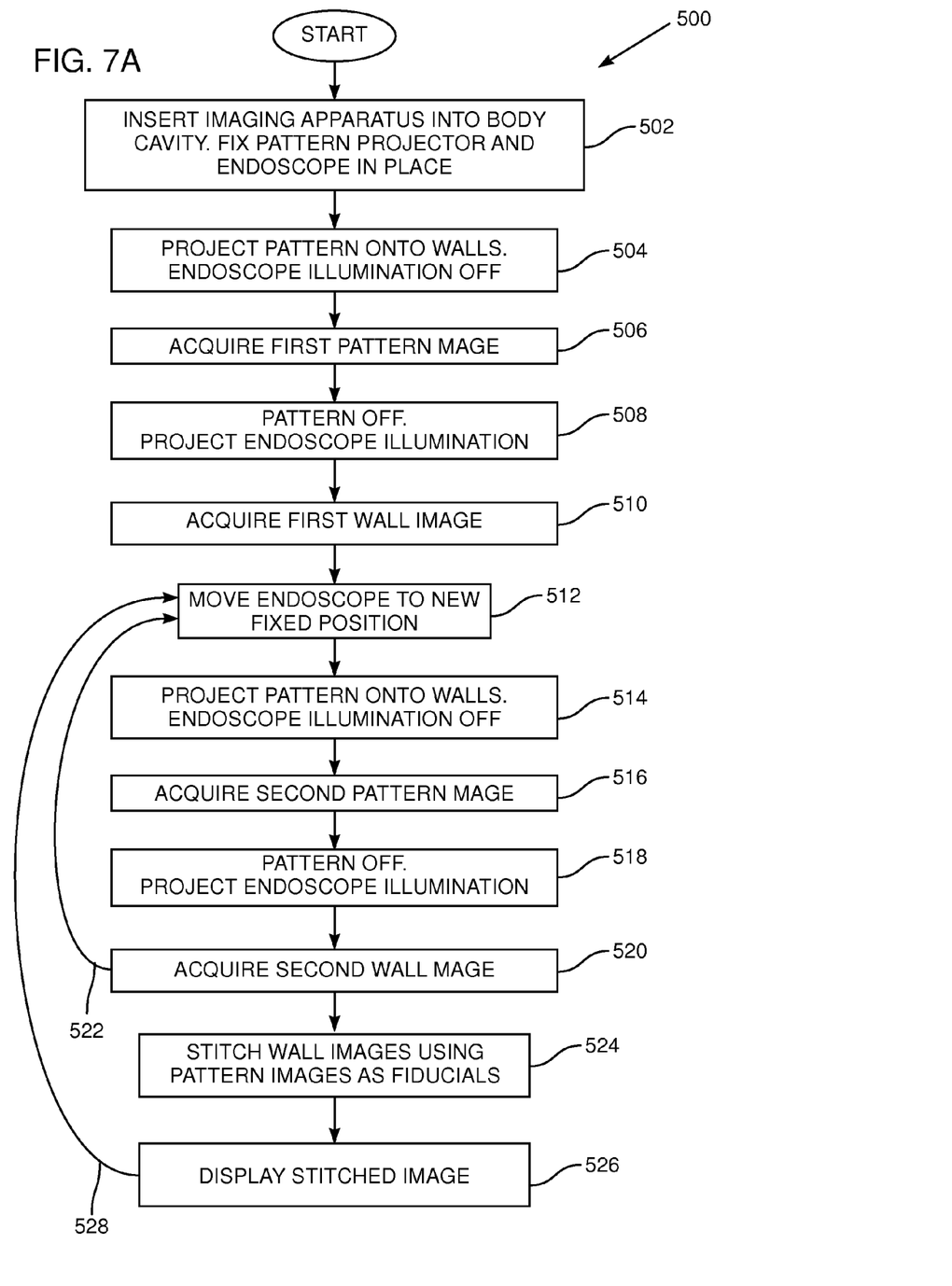
FIG. 7A is a flowchart of steps performed in generating a panoramic image of a bladder and FIG. 7B shows schematic diagrams illustrating the steps of the flowchart, according to an alternative embodiment of the present invention.

As is apparent from the description above, during implementation of flowchart 400 the light from laser 68 used for projecting pattern 61, and the light from illumination device 180 used to acquire images of walls 62, may both be projected simultaneously. A flowchart 500, described below, illustrates an embodiment wherein the light projecting the pattern and the light used to acquire wall images are toggled.

It will be appreciated that the stitching implemented in step 414 typically requires that images overlap, and that overlap may be ensured as explained above for motion step 408, by the system operator selecting appropriate positions for endoscope 16 using screen 32. Alternatively, the images should be contiguous. In some embodiments, typically when following paths illustrated by arrows 412 or 420, processor 20 checks for overlap or contiguity, and may display a warning on screen 32 that some images possess neither property. Because of the unique pattern characteristics of pattern 61, described above with respect to FIG. 4, there is no requirement that images acquired sequentially in time overlap or be contiguous. Rather, each image used to generate the panorama should overlap, or be contiguous with, or at least one other image that has been captured at any time of the acquisition process. The unique characteristics of pattern 61 ensure no ambiguity in stitching such images.

Figure 7B:
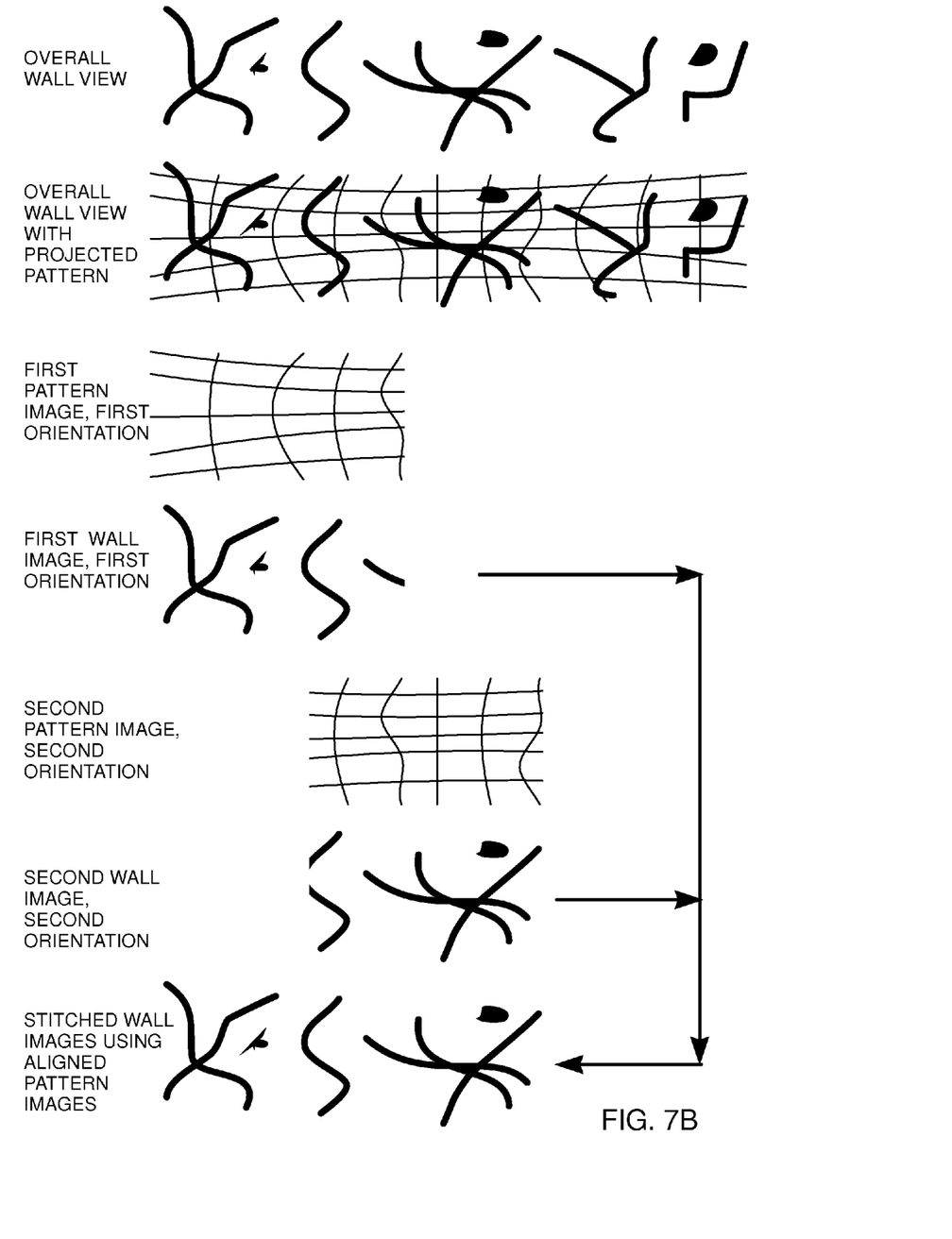

FIG. 7A is a flowchart 500 of steps performed in generating a panoramic image of bladder 12, and FIG. 7B shows schematic diagrams illustrating the steps of the flowchart, according to an alternative embodiment of the present invention. As for flowchart 400, the following description assumes that imaging apparatus 14 (FIG. 1 and FIG. 2A) is used to acquire images of the bladder, and that imaging section 90 of the apparatus is as described above with reference to FIG. 3A. The description also assumes that imaging device 160 is sensitive to the light projected by illumination device 180 and to the light from laser 68. Those having ordinary skill on the art will be able to adapt the description of flowchart 500, mutatis mutandis, if either imaging apparatus 114 or imaging apparatus 314 is used.

An "overall wall view" diagram (FIG. 7B) schematically illustrates walls 62, if they would be illuminated only by device 180. An "overall wall view with projected pattern" diagram illustrates walls 62 if they would be illuminated by device 180 and if pattern 61 would be projected on the walls.

As is explained further below, laser 68 and device 180 are toggled, i.e., they are switched intermittently so that when one is on, the other is off. Consequently, in contrast to the light requirements for flowchart 400, in implementation of flowchart 500 the wavelengths of light from laser 68 and from device 180 may be the same, or alternatively the wavelengths may be different.

A first step 502 is substantially the same as step 402 (FIG. 6).

In a first pattern projection step 504 laser 68 is activated to project pattern 61, so that the pattern formed on walls 62 is immobile and invariant. However, illumination device 180 is maintained in an off state. In a first pattern imaging step 506, imaging device 160, in its first orientation formed in step 502, acquires a first image of the projected pattern that is in field of view 168, and processor 20 stores the acquired first pattern image.

A "first pattern image, first orientation" (FIG. 7B) diagram illustrates the image acquired by device 160 in step 506.

In a first illumination step 508, pattern generating laser 68 is toggled off, and illumination device 180 is toggled on. In a first wall imaging step 510, imaging device 160 acquires a first wall image of a section of walls 62 in field of view 168, and processor 20 stores the acquired first wall image.

A "first wall image, first orientation" diagram illustrates the image acquired by device 160 in step 510.

A motion step 512 is substantially the same as motion step 408 (FIG. 6).

A second pattern projection step 514, a second pattern imaging step 516, a second illumination step 518, and a second wall imaging step 520 are respectively substantially the same as steps 504, 506, 508, and 510 described above. As for steps 504, 506, 508, and 510, in steps 514, 516, 518, and 520 the pattern and the wall illumination are toggled. In step 516 a second pattern image is acquired and stored; in step 520 a second wall image is acquired and stored. The second pattern image and the second wall image are acquired using the same field of view of imaging device 160. It will be understood that because of the different position and orientation of endoscope 16 engendered by motion step 512, the fields of view for the set of steps 504, 506, 508, and 510 and for the set of steps 514, 516, 518, and 520 are different.

A "second pattern image, second orientation" diagram illustrates the image acquired by device 160 in step 516, and a "second wall image, second orientation" diagram illustrates the image acquired by device 160 in step 520.

An arrow 522 illustrates that steps 512-520 are repeated. During the repetition, the pattern and the illumination light are toggled. At each new position of the endoscope (after implementation of step 512) a pattern image is acquired and a wall image is acquired.

In a stitching step 524 processor 20 stitches the first and second wall images, i.e., the wall images acquired in steps 510 and 520, to produce a panoramic image of walls 62. To accomplish the stitching the processor aligns a first given wall image with a second given wall image. The processor determines the alignment required for the two wall images by finding the alignment required to fit the corresponding pattern images, so that processor 20 uses the pattern images as fiducials for aligning the wall images.

A "stitched wall images using aligned pattern images" diagram illustrates the result of stitching step 524.

In a presentation step 526, processor 20 presents the stitched panoramic image on screen 32. If required, the system operator may return the flowchart to motion step 512, as illustrated by an arrow 528.

Figure 8:
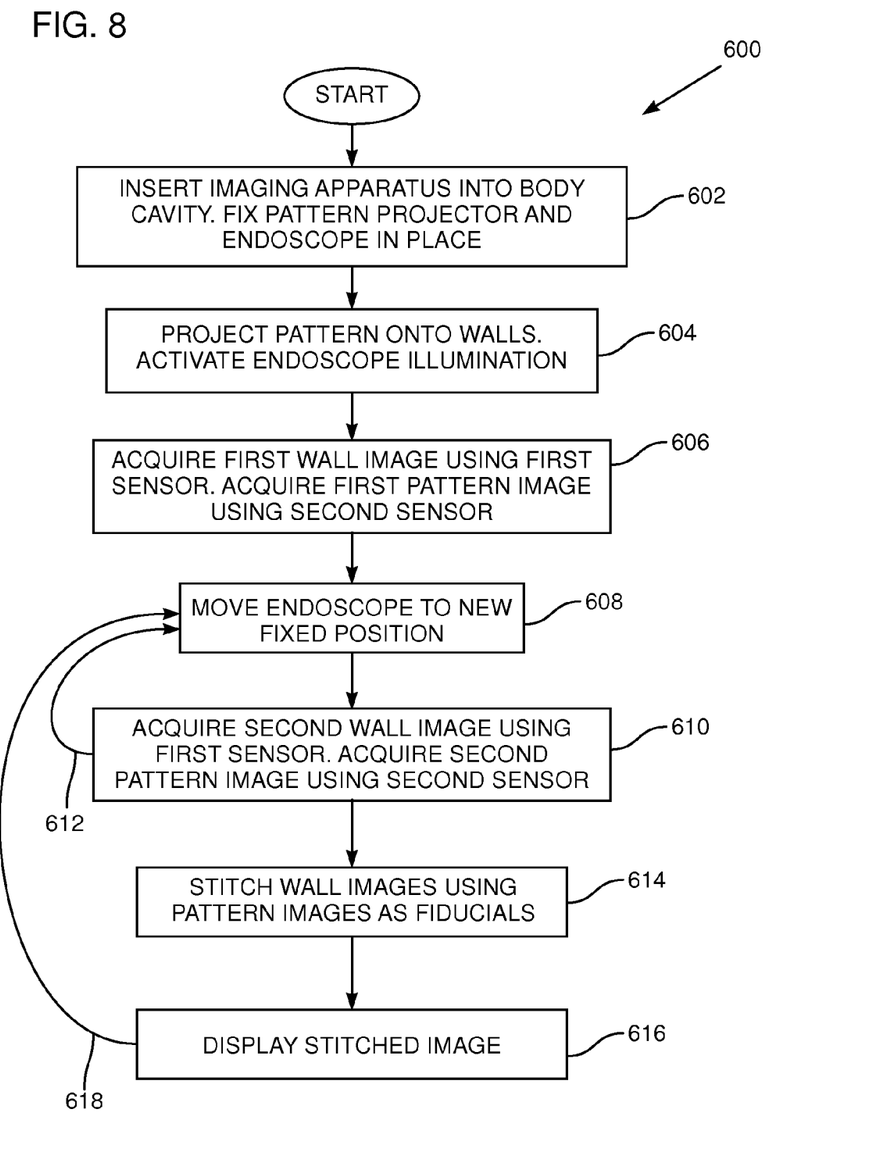
FIG. 8 is a flowchart of steps performed in generating a panoramic image of a bladder, according to a further alternative embodiment of the present invention.

FIG. 8 is a flowchart 600 of steps performed in generating a panoramic image of bladder 12, according to a further alternative embodiment of the present invention. The following description assumes that imaging apparatus 14 (FIG. 1 and FIG. 2A) is used to acquire images of the bladder, and that imaging section 290 of the apparatus is as described above with reference to FIG. 3B.

As is described above with reference to FIG. 3B, section 290 comprises two image devices 160 and 292. In the following description it is assumed that imaging device 160 is configured to be sensitive to light from illumination device 180, and to be insensitive to light from laser 68. In addition, imaging device 292 is configured to be sensitive to light from laser 68, and to be insensitive to light from illumination device 180. The wavelengths of the light from laser 68 and device 180 are substantially as described above for flowchart 400. Typically light from laser 68 is invisible, such as being in the infra-red region, whereas illumination device 180 projects visible light, typically white light.

An initial step 602 and an activation step 604 are generally as described above for steps 402 and 404 (FIG. 6) respectively. As for flowchart 400, in flowchart 600 the light from laser 68 and from illumination device 180 may be projected simultaneously. In the following description, simultaneous projection from laser 68 and device 180 is assumed. However, those with ordinary skill in the art will be able to adapt the description, mutatis mutandis, for the case of sequential projection, i.e., toggling, of the laser and the device, such as is described above with reference to flowchart 500.

In a first imaging step 606, imaging device 160 acquires a first wall image of a section of walls 62. Simultaneously, imaging device 292 acquires a first pattern image that is projected onto the section. The two first images have the same field of view 168, for a first orientation of the imaging device, and processor 20 stores the two first images.

A motion step 608 is substantially the same as motion step 408 (FIG. 6).

In a second imaging step 610, imaging device 160 acquires a second wall image of a section of walls 62. Simultaneously, imaging device 292 acquires a second pattern image that is projected onto the section. The two images have the same field of view 168 as each other, but because the endoscope has moved in step 608 to a second orientation, the two fields of view, and thus the sets of first and second images, are different.

As illustrated by an arrow 612, steps 608 and steps 610 are repeated, so that the process of moving endoscope 16 to a new fixed position, and capturing two images—a pattern image and a wall image—at the new position, iterates. The iterations typically acquire multiple sets of the two images, and may be repeated until the image displayed in a step 616 (described further below) is accepted by the system 10 operator.

In a stitching step 614 processor 20 stitches the first and second wall images, using the first and second images of pattern 61 as fiducials for performing the stitching. The stitching is generally as described above for step 524 (FIG. 7).

In a presentation step 616, processor 20 presents the stitched panoramic image on screen 32. If required, the system operator may return the flowchart to motion step 608, as illustrated by an arrow 618.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An imaging apparatus, comprising:
a pattern projecting device configured when in use to project a pattern onto a wall of a body cavity, wherein the pattern comprises at least a first section and a second section;
an illumination device configured to direct an illumination light onto the wall of the body cavity;
an imaging device configured when in use and while in a first orientation directed to the first section of the pattern projected onto the wall, to acquire a first pattern image of the first section of the projected pattern and a first wall image of the wall of the body cavity under the illumination light, and when in use and while in a second orientation directed to the second section of the pattern projected onto the wall, to acquire a second pattern image of the second section of the projected pattern and a second wall image of the wall of the body cavity under the illumination light; and a processor, which switches between the pattern projecting device and the illumination device intermittently so as to toggle the pattern projecting device and the illumination device such that the imaging device acquires the first and the second pattern images during the use of the pattern projecting device and acquires the first and the second wall images during the use of the illumination light, and stitches the first wall image to the second wall image using the first pattern image and the second pattern image.

2. The apparatus according to claim 1, wherein the pattern and the illumination light comprise visible light.

3. The apparatus according to claim 1, wherein the pattern is configured so that at least one of the first and second pattern images defines a unique direction of view of the imaging device.

4. The apparatus according to claim 3, wherein the pattern is configured so that the at least one of the first and second pattern images defines a unique orientation of the imaging device.

5. The apparatus according to claim 1, wherein the pattern projecting device comprises a light guide and a diffractive optic element.

6. The apparatus according to claim 1, wherein the illumination device comprises a light guide and a light source.

7. The apparatus according to claim 1, wherein the imaging device comprises an endoscope.

8. The apparatus according to claim 1, wherein the imaging device comprises a first sensor responsive to a first wavelength and a second sensor responsive to a second wavelength different from the first wavelength, and wherein the pattern projecting device is configured to project the pattern at the first wavelength and wherein the illumination device is configured to generate the illumination light at the second wavelength.

9. The apparatus according to claim 1, wherein the pattern projecting device is fixed in a given position so that the pattern projected onto the wall is immobile.

* * * * *